United States Patent
Nakagawa et al.

(10) Patent No.: US 10,190,921 B2
(45) Date of Patent: Jan. 29, 2019

(54) INTERNAL TEMPERATURE MEASUREMENT DEVICE

(71) Applicant: OMRON Corporation, Kyoto (JP)

(72) Inventors: Shinya Nakagawa, Shiga (JP); Masao Shimizu, Shiga (JP); Tsuyoshi Hamaguchi, Shiga (JP)

(73) Assignee: OMRON Corporation, Kyoto (JP)

( * ) Notice: Subject to any disclaimer, the term of this patent is extended or adjusted under 35 U.S.C. 154(b) by 135 days.

(21) Appl. No.: 15/509,397

(22) PCT Filed: Oct. 19, 2015

(86) PCT No.: PCT/JP2015/079437
§ 371 (c)(1),
(2) Date: Mar. 7, 2017

(87) PCT Pub. No.: WO2016/067952
PCT Pub. Date: May 6, 2016

(65) Prior Publication Data
US 2017/0276553 A1    Sep. 28, 2017

(30) Foreign Application Priority Data
Oct. 27, 2014 (JP) .................................. 2014-218441

(51) Int. Cl.
*A61B 5/01* (2006.01)
*G01K 7/28* (2006.01)
(Continued)

(52) U.S. Cl.
CPC .............. *G01K 13/002* (2013.01); *A61B 5/01* (2013.01); *B81B 3/0081* (2013.01);
(Continued)

(58) Field of Classification Search
CPC .. A61B 5/01; A61B 2562/0271; G01K 7/028; G01K 7/00; G01K 7/02; G01K 7/427;
(Continued)

(56) References Cited

U.S. PATENT DOCUMENTS

2002/0150143 A1   10/2002   Tokita et al.
2002/0191675 A1   12/2002   Tokita et al.
(Continued)

FOREIGN PATENT DOCUMENTS

CN    1380536 A    11/2002
CN    1392397 A    1/2003
(Continued)

OTHER PUBLICATIONS

Office Action issued in Chinese Application No. 201580048094.2, dated Jun. 14, 2018 (11 pages).
(Continued)

*Primary Examiner* — Gail Kaplan Verbitsky
(74) *Attorney, Agent, or Firm* — Osha Liang LLP

(57) ABSTRACT

Provided is an internal temperature measurement device capable of measuring an internal temperature of a measuring object for which the thermal resistance value of a non-heating body present on the surface side of the object is unknown, more accurately with better responsiveness than hitherto. The internal temperature measurement device 10 includes a MEMS chip 12 including: two cells 20a, 20b for measuring two heat fluxes for calculating an internal temperature of a measuring object for which the thermal resistance value of a non-heating body is unknown; and a cell 20c for increasing a difference between the heat fluxes.

3 Claims, 8 Drawing Sheets

(51) Int. Cl.
  *G01K 13/00* (2006.01)
  *B81B 3/00* (2006.01)
  *B81B 7/00* (2006.01)
  *G01K 7/02* (2006.01)
  *G01K 7/42* (2006.01)

(52) U.S. Cl.
  CPC ............ B81B 7/0019 (2013.01); G01K 7/028 (2013.01); G01K 7/427 (2013.01)

(58) Field of Classification Search
  CPC ...... G01K 13/002; G01K 17/06; G01K 5/486; G01K 2207/06; G01N 29/2437; G01N 30/6095
  USPC ............................ 374/29, 137, 163, 100, 179
  See application file for complete search history.

(56) References Cited

U.S. PATENT DOCUMENTS

| | | |
|---|---|---|
| 2005/0163190 A1 | 7/2005 | Tokita et al. |
| 2005/0220170 A1 | 10/2005 | Tokita et al. |
| 2015/0357375 A1* | 12/2015 | Tsai ........................ H01L 27/20 257/416 |
| 2016/0327523 A1* | 11/2016 | Shimoyama ........... H04R 23/02 |
| 2017/0168021 A1* | 6/2017 | Van Tooren ......... G01N 29/041 |
| 2018/0110415 A1* | 4/2018 | Sasahara .................. A61B 5/01 |

FOREIGN PATENT DOCUMENTS

| | | | |
|---|---|---|---|
| JP | S61-239127 A | 10/1986 | |
| JP | 2007-212407 A | 8/2007 | |
| JP | WO 2016143518 A1 * | 9/2016 | ............... A61B 5/01 |

OTHER PUBLICATIONS

International Search Report issued in PCT/JP2015/079437, dated Dec. 22, 2015 (2 pages).
Written Opinion of the International Searching Authority issued in PCT/JP2015/079437, dated Dec. 22, 2015 (3 pages).

\* cited by examiner (A)

(B)

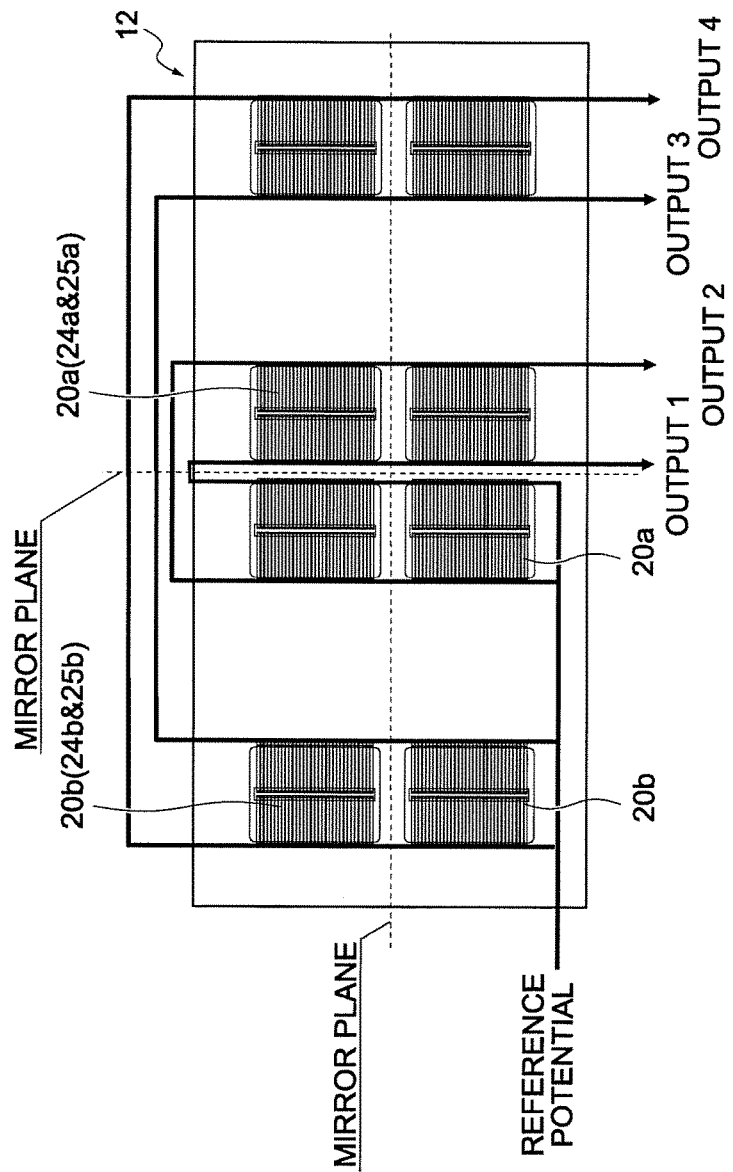

INTERNAL TEMPERATURE MEASUREMENT DEVICE

TECHNICAL FIELD

The present invention relates to an internal temperature measurement device configured to measure an internal temperature of a measuring object.

BACKGROUND ART

Known examples of devices configured to measure a deep body temperature include a device called non-heating simple deep body thermometer (hereinafter referred to as non-heating deep body thermometer) or the like is known.

Known examples of the non-heating deep body thermometer include a thermometer configured to measure a deep body temperature by using a single heat flux sensor obtained by mounting temperature sensors on top and bottom surfaces of a heat insulator having a relatively wide area and a thermometer configured to measure a deep body temperature by using two such heat flux sensors.

Referring to FIG. 1, the former non-heating deep body thermometer is first described.

For measurement of a deep body temperature with a non-heating deep body thermometer using a single heat flux sensor, the heat flux sensor is brought into intimate contact with the body surface as illustrated in FIG. 1(A).

As illustrated in FIG. 1(B), a temperature Tt of a heat insulator bottom surface measured by the heat flux sensor (temperature sensor closer to bottom surface of heat insulator) in intimate contact with the body surface is lower than a deep body temperature Tb. A temperature Ta of a heat insulator top surface measured by the heat flux sensor (temperature sensor closer to top surface of heat insulator) in intimate contact with the body surface is lower than the temperature Tt. A thermal equivalent circuit of the structure illustrated in FIG. 1(A) is expressed by FIG. 1(C). Rx and R1 are a thermal resistance value of subcutaneous tissue, which is a non-heating body, and a thermal resistance value of the heat insulator, respectively.

When the temperature of each part of the heat flux sensor in intimate contact with the body surface is stabilized, the quantity of heat passing through the non-heating body in a unit time and the quantity of heat passing through the heat insulator in a unit time becomes equal to each other. Specifically, when the temperature of each part of the heat flux sensor is stabilized, Equation (1) is established.

$$(Tb-Tt)/Rx = (Tt-Ta)/R1 \quad (1)$$

Thus, when the temperature of each part of the heat flux sensor is stabilized, the deep body temperature Tb can be calculated by Equation (2) obtained by solving Equation (1) for Tb.

$$Tb = Tt + (Tt-Ta) \cdot Rx/R1 \quad (2)$$

The non-heating deep body thermometer of the type using a single heat flux sensor is configured to calculate the deep body temperature Tb by Equation (2). The Rx value, however, differs depending on location and differs among individuals. The deep body temperature Tb calculated by Equation (2) using a fixed value as the Rx value thus includes a measurement error corresponding to a difference between the Rx value used and the actual Rx value.

A non-heating deep body thermometer developed such that the measurement error is prevented from being included in the measurement result of the deep body temperature Tb is a non-heating deep body thermometer of a type configured to measure a deep body temperature by using two heat flux sensors (see, for example, PTL 1).

For measurement of a deep body temperature with this type of non-heating deep body thermometer, two heat flux sensors are brought into intimate contact with the body surface as illustrated in FIG. 2(A).

As illustrated in FIGS. 2(A) and 2(B), a temperature of a heat insulator top surface and a temperature of a heat insulator bottom surface measured by a thermal resistance value of a heat insulator in one heat flux sensor (hereinafter referred to as first heat flux sensor) are referred to as Ta and Tt, respectively, and a temperature of the heat insulator top surface and a temperature of the heat insulator bottom surface measured by the other heat flux sensor (hereinafter referred to as second heat flux sensor) are referred to as Ta' and Tt', respectively. In this case, a thermal equivalent circuit of the structure illustrated in FIG. 2(A) is expressed by FIG. 2(C). Rx, R1, and R2 are a thermal resistance value of subcutaneous tissue, which is a non-heating body, a thermal resistance value of the heat insulator in the first heat flux sensor, and a thermal resistance value of the heat insulator in the second heat flux sensor, respectively.

Thus, Equation (2) is established for the first heat flux sensor, and Equation (3) is established for the second heat flux sensor.

$$Tb = Tt' + (Tt'-Ta') \cdot RX/R2 \quad (3)$$

Eliminating Rx from Equations (2) and (3) enables Equation (4) to be obtained.

[Math. 1]
$$Tb = \frac{R2 \cdot \Delta T \cdot Tt' - R1 \cdot \Delta T' \cdot Tt}{R2 \cdot \Delta T - R1 \cdot \Delta T'} \quad (4)$$

The use of a ratio k (=R2/R1) of R2 to R1 enables Equation (4) to be transformed to Equation (5).

[Math. 2]
$$Tb = \frac{k \cdot \Delta T \cdot Tt' - \Delta T' \cdot Tt}{k \cdot \Delta T - \Delta T'} \quad (5)$$

The non-heating deep body thermometer of the type using two heat flux sensors is configured to calculate the deep body temperature Tb by Equation (4) or Equation (5).

CITATION LIST

Patent Literature

PTL 1: Japanese Patent Application Publication No. 2007-212407

SUMMARY OF INVENTION

Technical Problem

The non-heating deep body thermometer of the type using two heat flux sensors enables the deep body temperature Tb to be relatively accurately measured (calculated), regardless of the Rx value of a measurement subject of the deep body temperature Tb. The existing non-heating deep body thermometer is, however, configured such that information necessary to calculate the internal temperature Tb is acquired from four temperature sensors as described above (see FIG. 2). The accuracy of the temperature sensors is not so high, and hence the existing non-heating deep body thermometer employs a heat insulator having a large thermal resistance and a large heat capacity, with the result that the existing non-heating deep body thermometer has poor responsiveness (it takes time to obtain stable measurement result of deep body temperature). Depending on cases, the existing non-heating deep body thermometer has a large error due to individual differences of temperature sensors in the deep body temperature measurement result.

It is therefore an object of the present invention to provide an internal temperature measurement device capable of measuring an internal temperature of a measuring object for which the thermal resistance value of a non-heating body present on the surface side of the object is unknown, more accurately with better responsiveness than hitherto.

Solution to Problem

In order to solve the above-mentioned problems, an internal temperature measurement device of the present invention includes: a base portion, one surface of which is to be brought into contact with a surface of a measuring object when an internal temperature of the measuring object is measured; a MEMS chip arranged on another surface of the base portion and including: a substrate portion including a first thin film portion and a second thin film portion that are hollow on the base portion side; a first thermopile configured to measure a first temperature difference between a predetermined region and another region of the first thin film portion; and a second thermopile configured to measure a second temperature difference between a predetermined region and another region of the second thin film portion; and a calculation unit configured to calculate an internal temperature of the measuring object by using the first temperature difference measured by the first thermopile and the second temperature difference measured by the second thermopile, wherein the MEMS chip is configured such that a first heat flux which passes through the predetermined region of the first thin film portion from the measuring object in contact with the one surface of the base portion, and which is determined on the basis of the first temperature difference, and a second heat flux which passes through the predetermined region of the second thin film portion from the measuring object in contact with the one surface of the base portion, and which is determined on the basis of the second temperature difference, are different from each other, and in order to reduce the first heat flux, a thin film portion that is hollow on the base portion side is provided on at least one of both sides of the first thin film portion of the substrate portion in a direction where the first thin film portion and the second thin film portion are arranged.

Specifically, the internal temperature measurement device of the present invention is configured to acquire a temperature difference used to calculate an internal temperature from two thermopiles in a micro electro mechanical systems (MEMS) chip. The use of thermopiles enables the temperature difference to be measured with higher accuracy than when two temperature sensors are used. Because a plurality of temperature sensors are not used, errors (individual differences) of the temperature sensors are prevented from being added to increase the error. The MEMS chip has a small heat capacity (becomes a thermal equilibrium state in a short period of time). The internal temperature measurement device of the present invention can thus measure an internal temperature of a measuring object for which the thermal resistance value of a non-heating body present on the surface side of the object is unknown, more accurately with better responsiveness than hitherto.

When the magnitude of the first heat flux and the magnitude of the second heat flux are close to each other, the internal temperature calculation result by the calculation unit is not stabilized. The MEMS chip in the internal temperature measurement device of the present invention has a configuration in which a thin film portion that is hollow on the base portion side is provided on at least one of both sides of the first thin film portion of the substrate portion in a direction where the first thin film portion and the second thin film portion are arranged. The MEMS chip having such a configuration decreases the first heat flux to increase the difference between the first heat flux and the second heat flux ("first heat flux/second heat flux" is decreased). Consequently, in the internal temperature measurement device of the present invention, the calculation result of the internal temperature by the calculation unit is stabilized.

Increasing the magnitude of the first thin film portion enables the magnitude of the first heat flux and the magnitude of the second heat flux to be different from each other. Note that when the magnitude of the first thin film portion is increased, the strength of the first thin film portion is reduced and a MEMS chip having a fragile first thin film portion is obtained. On the other hand, employing "a configuration in which a thin film portion that is hollow on the base portion side is provided on at least one of both sides of the first thin film portion of the substrate portion in a direction where the first thin film portion and the second thin film portion are arranged" for the MEMS chip enables the magnitude of the first heat flux and the magnitude of the second heat flux to be different from each other without increasing the magnitude of the first thin film portion. Thus, it can be said that the internal temperature measurement device of the present invention including the MSMS chip having the above-mentioned configuration is a device that is resistant to impact and is easily manufactured such that the internal temperature estimation result is stabilized.

The internal temperature measurement device of the present invention may be implemented as a device in which each unit is housed in a single casing or a device in which two devices (for example, a device including units other than the calculation unit and a device including the calculation unit) are connected via a cable. The base portion in the internal temperature measurement device of the present invention may be a single-layer member or a multi-layer member (such as a laminate in which a biocompatible insulating film, resin member or the like is disposed on the surface on the measuring object side).

The internal temperature measurement device of the present invention may employ a MEMS chip which is configured such that it has a first mirror plane perpendicular to the direction where the first thin film portion and the second thin film portion are arranged and which is configured such that the first thin film portion, the second thin film portion, the first thermopile and the second thermopile are included in each part sectioned by the first mirror plane and that the first thin film portion in each part is adjacent to the first mirror plane. When the MEMS chip has such a configuration, the first thin film portion in each part functions as "thin film portion" configured to reduce the first heat flux from the first thin film portion in another part. When the MEMS chip employs the above-mentioned configuration, a "thin film portion" may be provided separately from the first thin film portion in each part.

In order to prevent an increase in error of the internal temperature estimation result even when contact between a part of the bottom surface ("one surface") of the base portion and the surface of the measuring object is poor, the internal temperature measurement device of the present invention may employ a configuration in which "the MEMS chip is configured such that it has a first mirror plane and a second mirror plane orthogonal to the first mirror plane, the first thin film portion, the second thin film portion, the first thermopile and the second thermopile are included in each part sectioned by the first and second mirror planes, and the first thin film portion in each part is adjacent to the first mirror plane and the second mirror plane; and the calculation unit calculates the internal temperature of the measuring object by using an average value of first temperature differences measured by four first thermopiles in the MEMS chip and an average value of second temperature differences measured by four second thermopiles in the MEMS chip".

Advantageous Effects of Invention

According to the present invention, an internal temperature of a measuring object can be measured more accurately with better responsiveness than hitherto.

BRIEF DESCRIPTION OF DRAWINGS

FIG. 8 is an explanatory diagram of the configuration and functions of a MEMS chip (third MEMS chip) included in an internal temperature measurement device according to a third embodiment of the present invention.

DESCRIPTION OF EMBODIMENTS

Referring to the accompanying drawings, embodiments of the present invention are described below.

First Embodiment

Figure 3:
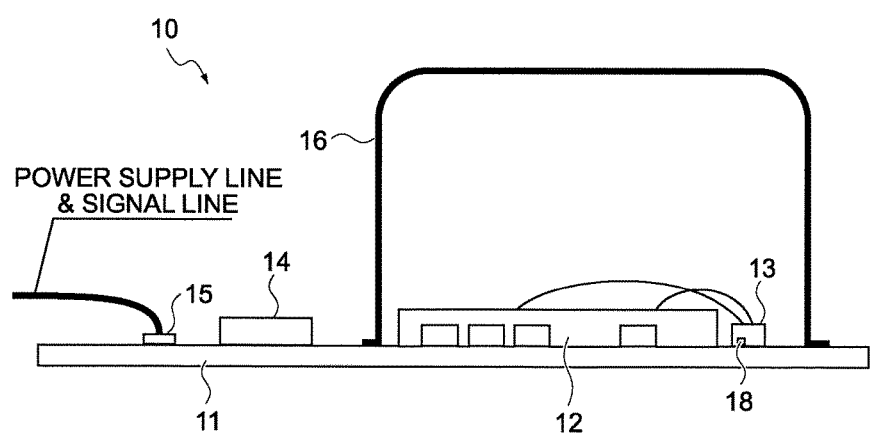
FIG. 3 is a schematic configuration diagram of an internal temperature measurement device according to a first embodiment of the present invention.

FIG. 3 illustrates a schematic configuration of an internal temperature measurement device 10 according to a first embodiment of the present invention.

As illustrated in FIG. 3, the internal temperature measurement device 10 includes a base portion 11, and a micro electro mechanical systems (MEMS) chip 12, an application specific integrated circuit (ASIC) 13, an arithmetic circuit 14, and a terminal 15 that are disposed on the base portion 11. The internal temperature measurement device 10 further includes a housing 16 that is disposed on the base portion 11 such that the MEMS chip 12 and the ASIC 13 are housed therein.

Figure 1:
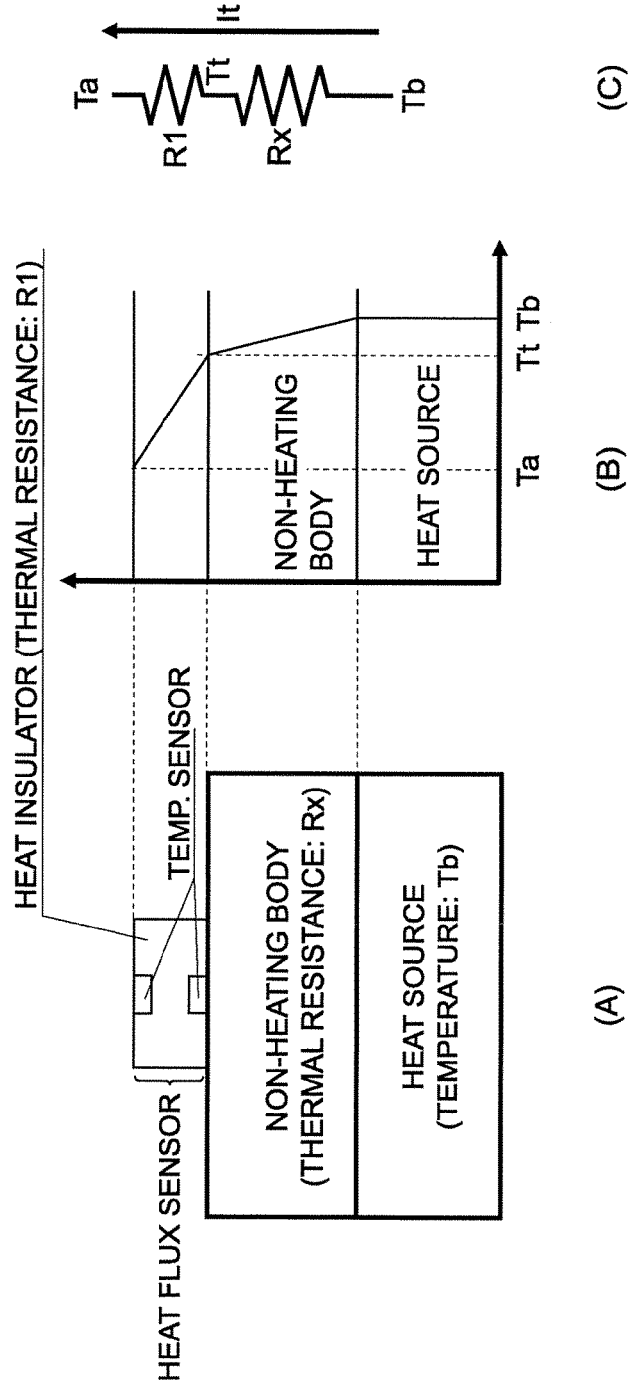
FIG. 1 is an explanatory diagram of an existing non-heating deep body thermometer using a single heat flux sensor.

The base portion 11 is a member on which wiring among the ASIC 13, the arithmetic circuit 14, and the terminal 15 is formed. For use of the internal temperature measurement device 10, the bottom surface of the base portion 11 (lower surface in FIG. 1) is brought into contact with the surface of an object, the internal temperature of which is to be measured. The base portion 11 may be either of a single-layer member or a laminate in which a biocompatible insulating film, resin member or the like is disposed on the bottom surface side.

The terminal 15 is a terminal connected to a power supply line and a signal line from an instrumentation device for the internal temperature measurement device 10. The instrumentation device for the internal temperature measurement device 10 refers to a device having, for example, the function of acquiring an internal temperature measurement result from the internal temperature measurement device 10 through communication with the internal temperature measurement device 10 via the signal line, the function of displaying and recording the acquired measurement result, and the function of supplying electric power to the internal temperature measurement device 10 via the power supply line.

The MEMS chip 12 is a device manufactured with MEMS technology. Details of the MEMS chip 12 are described later.

The ASIC 13 is an integrated circuit having a temperature sensor 18 built therein. The ASIC 13 has the function of amplifying an output of each sensor (temperature sensor 18 and output cells 20a and 20b described later) in the internal temperature measurement device 10 and the function of converting each amplified output into digital data. The ASIC 13 in the internal temperature measurement device 10 according to the present embodiment includes a proportional-to-absolute temperature (PTAT) voltage source configured to output a voltage proportional to an absolute temperature (that is, a voltage source that functions as a thermometer). Specifically, the ASIC 13 is a circuit in which the component of the PTAT voltage source functions as the temperature sensor 18.

The arithmetic circuit 14 is a circuit configured to calculate and output an internal temperature of a measuring object on the basis of a measurement value of each sensor input via the ASIC 13. A procedure of calculating the internal temperature by the arithmetic circuit 14 is described later. The arithmetic circuit 14 may be either of a circuit configured to output (transmit) the calculated internal temperature from the terminal 15 or a circuit configured to output (store) the calculated internal temperature in an internal memory. The arithmetic circuit 14 may be either of a single element (such as integrated circuit) or a unit formed of a plurality of elements. The arithmetic circuit 14 may be either of a programmable element or unit or an unprogrammable element or unit.

The housing 16 is a member provided for the purposes of, for example, stabilizing the output of each sensor by fixing the air around the MEMS chip 12 and the temperature sensor 18, and preventing infrared rays from entering each output cell 20 from above.

The housing 16 may use any constituent material that can prevent the inflow and outflow of air to and from the housing 16 and the incidence of infrared rays into the housing 16.

The output of each sensor can fluctuate by electromagnetic waves. It is therefore preferred that the constituent material of the housing 16 be a material that can also prevent the incidence of electromagnetic waves from the outside, that is, metal or non-metal having conductivity. The housing 16 may be either of a single member or a combination of a plurality of members. The inner surface of the housing 16 may be covered with an infrared absorber (such as black resin) in order to improve the stability of temperature in the housing 16.

The configuration of the MEMS chip 12 is described below. In the following description, "top", "bottom", "left", and "right" in each portion (such as MEMS chip 12) respectively refer to "top", "bottom", "left", and "right" in each portion in the state illustrated in FIG. 3. Further, "front" and "rear" respectively refer to "near side" and "far side" when viewed from the direction perpendicular to the sheet of FIG. 3.

Figure 4:
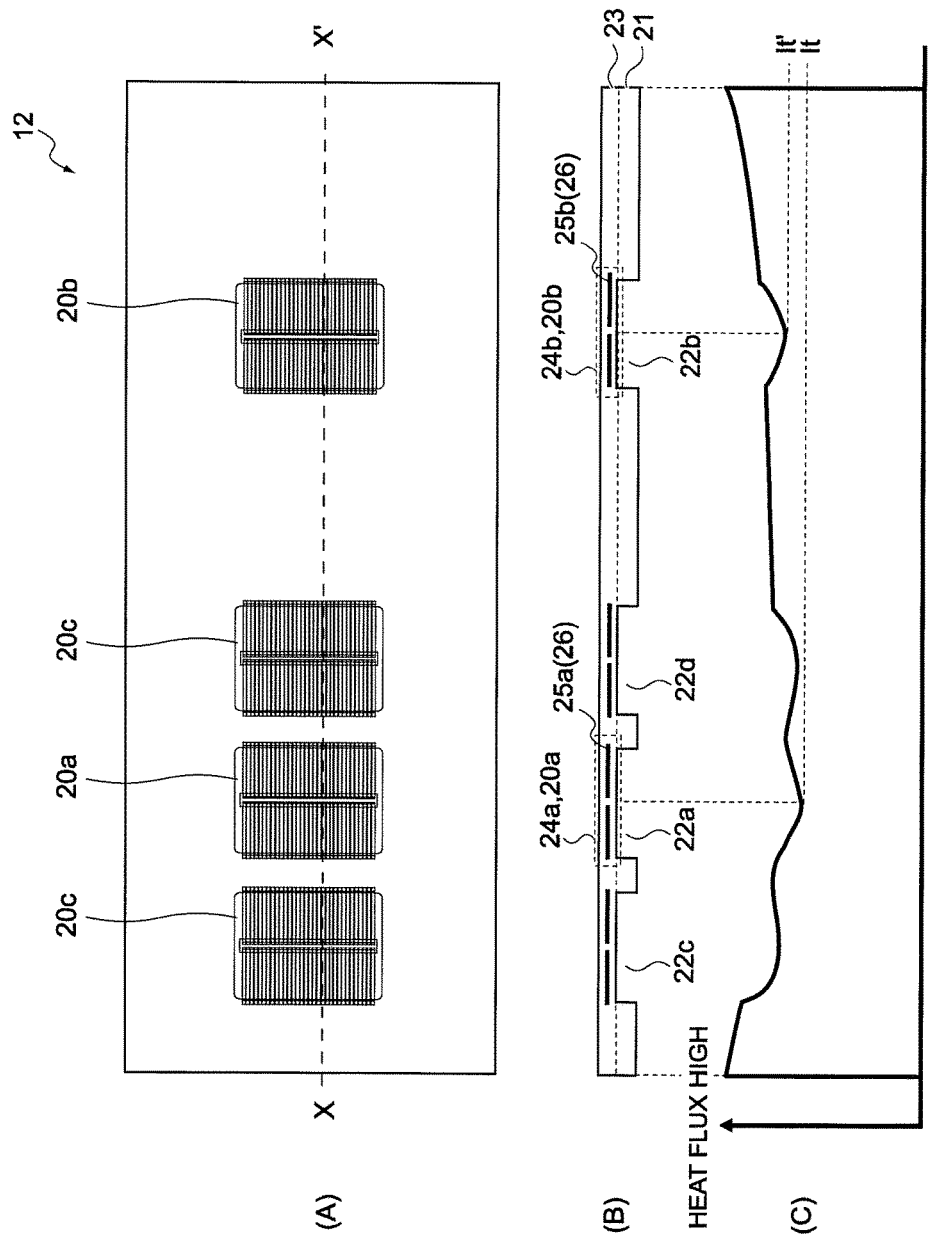
FIG. 4 is an explanatory diagram of the configuration and functions of a MEMS chip (first MEMS chip) included in the internal temperature measurement device according to the first embodiment.

FIG. 4(A) illustrates a top view of the MEMS chip 12, and FIG. 4(B) is a cross-sectional view of the MEMS chip 12 taken along the line X-X' in FIG. 4(A). FIG. 4(C) illustrates a distribution diagram of heat flux on the top surface of the MEMS chip 12, which is released upward from the vicinity of the cross-section taken along the line X-X' in FIG. 4(A).

As illustrated in FIGS. 4(A) and 4(B), the MEMS chip 12 has a configuration in which a laminate portion 23 is provided on a substrate (in the present embodiment, a silicon substrate) 21 having four opening portions 22a, 22b, 22c, and 22d with substantially the same shape formed therein.

A thermopile 25a is formed in a part of the laminate portion 23 that covers the opening portion 22a (hereinafter referred to as thin film portion 24a). A thermopile 25b is formed in a part of the laminate portion 23 that covers the opening portion 22b (hereinafter referred to as thin film portion 24b). A thermopile 25x in each thin film portion 24x (x=a, b) is a sensor in which a plurality of thermocouples 26 each obtained by laminating P-type polysilicon and N-type polysilicon are connected in series. The thermopile 25x is formed such that a cold junction of each thermocouple 26 is located at the lateral center part of the thin film portion 24x and hot junctions of each thermocouple 26 are located at right and left ends of the thin film portion 24x (portions on the substrate 21).

A part formed of the thin film portion 24x (x=a, b) and the thermopile 25x is hereinafter referred to as output cell 20x.

Output cells 20c having the same configuration as the output cells 20a and 20b are provided above the opening portions 22c and 22d.

Of the four output cells 20 included in the MEMS chip 12, the output cell 20a is a cell provided in order to measure a temperature difference $\Delta T$ ($\Delta T$ in proportion to It) representing a heat flux It that is released upward from the lateral center part of the output cell 20a. The output cell 20b is a cell provided in order to measure a temperature difference $\Delta T'$ representing a heat flux It' that is released upward from the lateral center part of the output cell 20b.

Two output cells 20c located on the left and right sides of the output cell 20a are cells provided in order to reduce the heat flux It (increase a difference between the heat flux It and the heat flux It'). Specifically, when the output cells 20c that are hollow (opening portions) on the base 11 side are present on the left and right sides of the output cell 20a, the quantity of heat that flows into the output cell 20a from the lateral direction (left-right direction) becomes smaller than that without the output cell 20c. Providing the output cells 20c on the left and right sides of the output cell 20a enables, as illustrated in FIG. 4(C), the heat flux It that is released from the center part of the output cell 20a having the same configuration as the output cell 20b to be smaller than the heat flux It' that is released from the center part of the output cell 20b.

Figure 2:
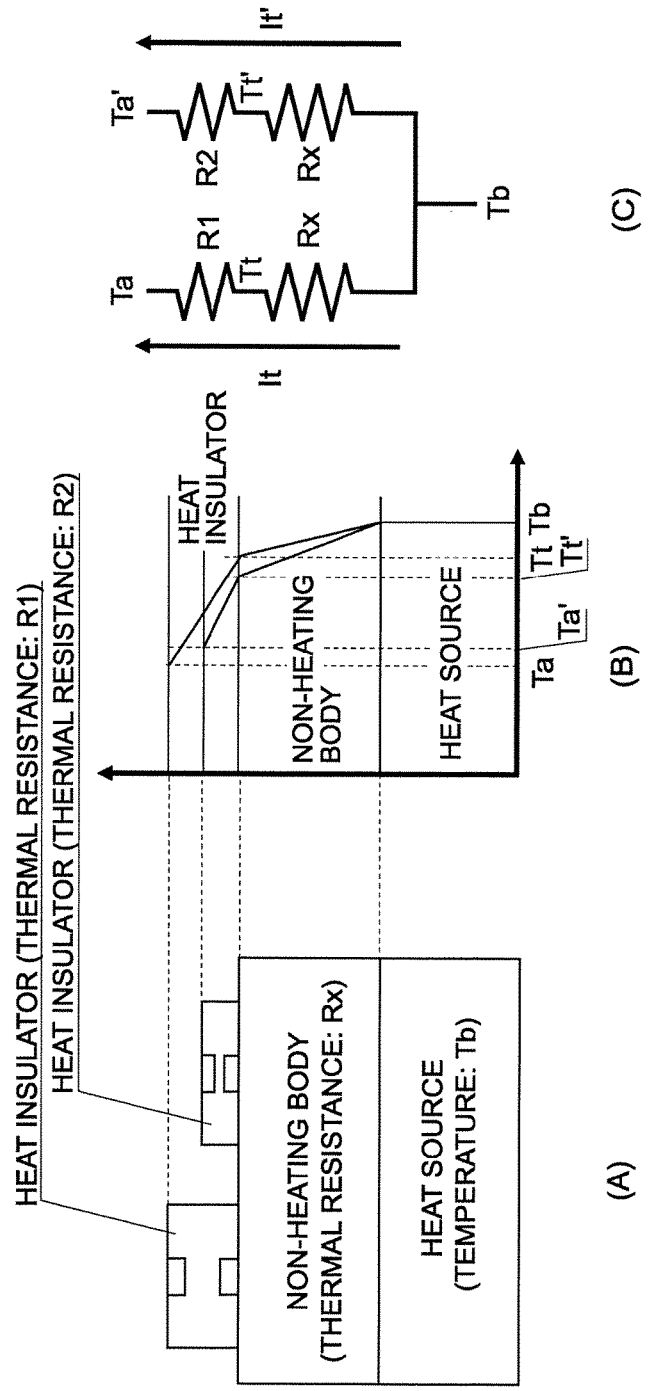
FIG. 2 is an explanatory diagram of an existing non-heating deep body thermometer using two heat flux sensors.

Acquiring two heat fluxes (two heat fluxes having different values) from the measuring object, which have passed through two paths having different thermal resistances, enables the internal temperature to be calculated by the internal temperature calculation principle described above with reference to FIG. 2. However, the internal temperature cannot be calculated by the above-mentioned internal temperature calculation principle simply with a temperature difference $\Delta T$ measured by the thermopile 25a, a temperature difference $\Delta T'$ measured by the thermopile 25b, a temperature measurement result by the temperature sensor 18, and known values.

It is therefore assumed that Ta=Ta' and Tt=Tr are established in the internal temperature measurement device 10 according to the present embodiment. Ta is temperature at a cold junction in the thermopile 25a, and Ta' is temperature at a cold junction in the thermopile 25b (temperature at the lateral center part of the output cell 20a). Tt is temperature at a hot junction in the thermopile 25a, and Tr is a temperature measurement result by the temperature sensor 18.

Assuming that Ta=Ta' and Tt=Tr are established enables the internal temperature Tb to be calculated by Equation (e1).

[Math. 3]

$$Tb = Tr + \frac{k(\Delta T' - \Delta T)\Delta T}{k \cdot \Delta T - \Delta T'} \qquad (e1)$$

where k is the ratio (=R2/R1) of the thermal resistance R2 of a portion at which the temperature difference $\Delta T'$ is measured by the thermopile 25b to the thermal resistance R1 of a portion at which the temperature difference $\Delta T$ is measured by the thermopile 25a. Equation (e1) becomes the same as Equation (5) when transformed with use of Ta=Ta', Tt=Tr, $\Delta T$=Tt-Ta, and $\Delta T'$=Tt'-Ta' (Tt' is temperature at a hot junction in the thermopile 25b).

Thus, the internal temperature measurement device 10 according to the present embodiment employs a circuit configured to calculate the internal temperature Tb by Equation (e1) as the arithmetic circuit 14.

The reason why the above-mentioned configuration (see FIG. 4) is employed for the MEMS chip 12 in the internal temperature measurement device 10 is now described.

$\Delta T$=R1·It and $\Delta T'$=R2·It' are established, and hence the following equation is established for "k·$\Delta T$-$\Delta T'$" of the denominator in the fractional term of the right side in Equation (e1).

$k \cdot \Delta T - \Delta T' = R2(It - It')$

Accordingly, if It-It' is a value close to "0", the internal temperature estimation result by Equation (e1) is not stabilized.

Figure 5:
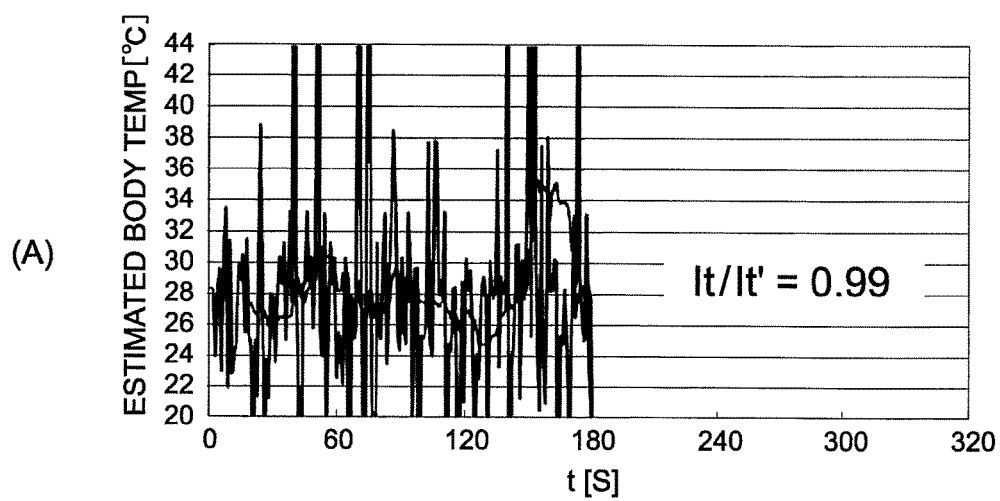
FIG. 5 is an explanatory diagram of influence of the value of It/It' on the output of the internal temperature measurement device.
Figure 5:
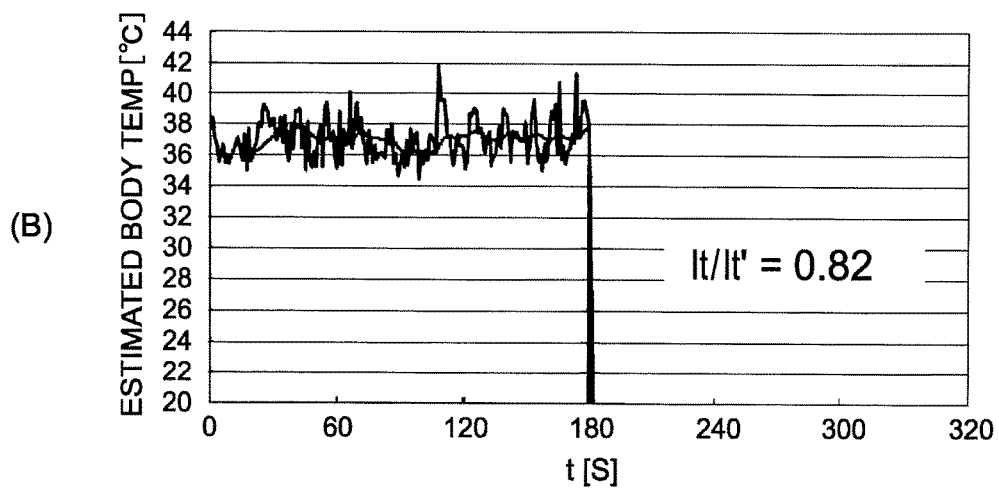

Specifically, when the MEMS chip 12 having It/It' of 0.99 is used, the output of the internal temperature measurement device 10 (estimation result of deep body temperature by the internal temperature measurement device 10) extremely greatly fluctuates as illustrated in FIG. 5(A). When the MEMS chip 12 having It/It' of 0.82 is used, on the other hand, the output of the internal temperature measurement device 10 does not greatly fluctuate (temporal average of the output can be used as deep body temperature) as illustrated in FIG. 5(B). The measurement results illustrated in FIGS. 5(A) and 5(B) are obtained by using an evaluation device simulating the human body with an internal temperature (deep body temperature) of 37° C.

As described above, the estimation result of the internal temperature Tb by Equation (e1) becomes more stable as the value of It/It' becomes smaller. It is therefore preferred that the MEMS chip 12 mounted on the internal temperature measurement device 10 have a relatively small value of It/It' (0.9 or less).

Figure 6:
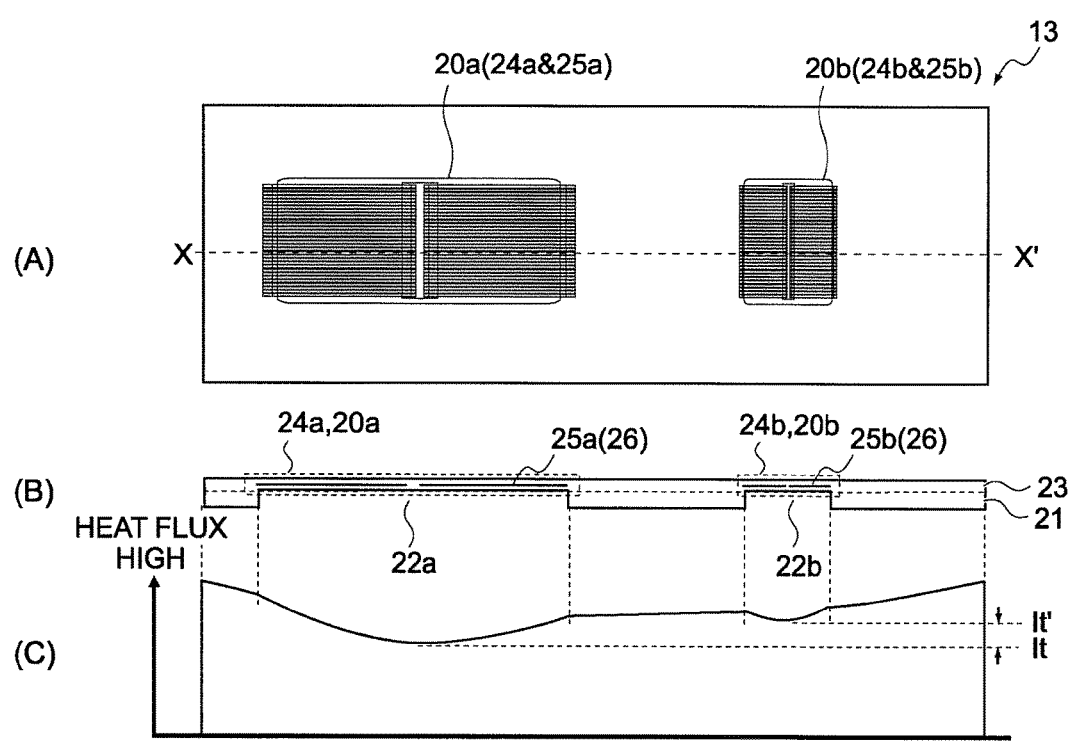
FIG. 6 is an explanatory diagram of a MEMS chip in which the value of It/It' is decreased by size adjustment of an output cell.

Employing the configuration illustrated in FIGS. 6(A) and 6(B), that is, the configuration in which the lateral length of the output cell 20a is larger than that of the output cell 20b, can obtain a MSM chip 13 having a relatively small value of It/It'. FIG. 6(A) is a top view of the MEMS chip 13, and FIG. 6(B) is a cross-sectional view of the MEMS chip 13 taken along the line X-X' in FIG. 6(A). FIG. 6(C) is a distribution diagram of heat flux on the top surface of the MEMS chip 13, which is released upward from the vicinity of the cross-section taken along the line X-X' in FIG. 6(A).

Increasing the lateral length of the output cell 20a in order to decrease It/It' may make the manufacturing of chips difficult and reduce the strength of the output cell 20a (thin film portion 24a).

Employing the configuration in which the output cells 20 are provided on the left and right sides of the output cell 20a, on the other hand, can decrease It/It' without making the manufacturing of chips difficult or reducing the strength of the output cell 20a. This is the reason why the above-mentioned configuration (see FIG. 4) is employed for the MEMS chip 12 in the internal temperature measurement device 10.

As described above, the internal temperature measurement device 10 according to the present embodiment is configured such that information to be used to calculate an internal temperature Tb of a measuring object is acquired from two thermopiles 25 in the MEMS chip 12 and the temperature sensor 18. The use of the thermopiles 25 can measure the temperature difference with higher accuracy than when two temperature sensors are used. Because a plurality of temperature sensors are not used, errors (individual differences) of the temperature sensors are prevented from being added to increase the error. The MEMS chip 12 has a small heat capacity (becomes a thermal equilibrium state in a short period of time). The use of the internal temperature measurement device 10 according to the present embodiment thus enables an internal temperature of a measuring object to be measured more accurately with better responsiveness than hitherto.

The MEMS chip 12 included in the internal temperature measurement device 10 can decrease It/It' without making the manufacturing of chips difficult or reducing the strength of the output cell 20a. Thus, it can be said that the internal temperature measurement device 10 according to the present embodiment including the MEMS chip 12 is a device that is resistant to impact and is easily manufactured such that the estimation result of the internal temperature Tb is stabilized.

Second Embodiment

Now, the configuration of an internal temperature measurement device 10 according to a second embodiment of the present invention is described with reference to the same symbols used above for the description of the internal temperature measurement device 10 according to the first embodiment. In the following description, the n-th (n=1 to 3) MEMS chip 12 refers to the MEMS chip 12 included in the internal temperature measurement device 10 according to the n-th embodiment.

The internal temperature measurement device 10 according to the present embodiment is obtained by replacing the first MEMS chip 12 (see FIG. 4) in the internal temperature measurement device 10 according to the first embodiment with a second MEMS chip 12.

Figure 7:
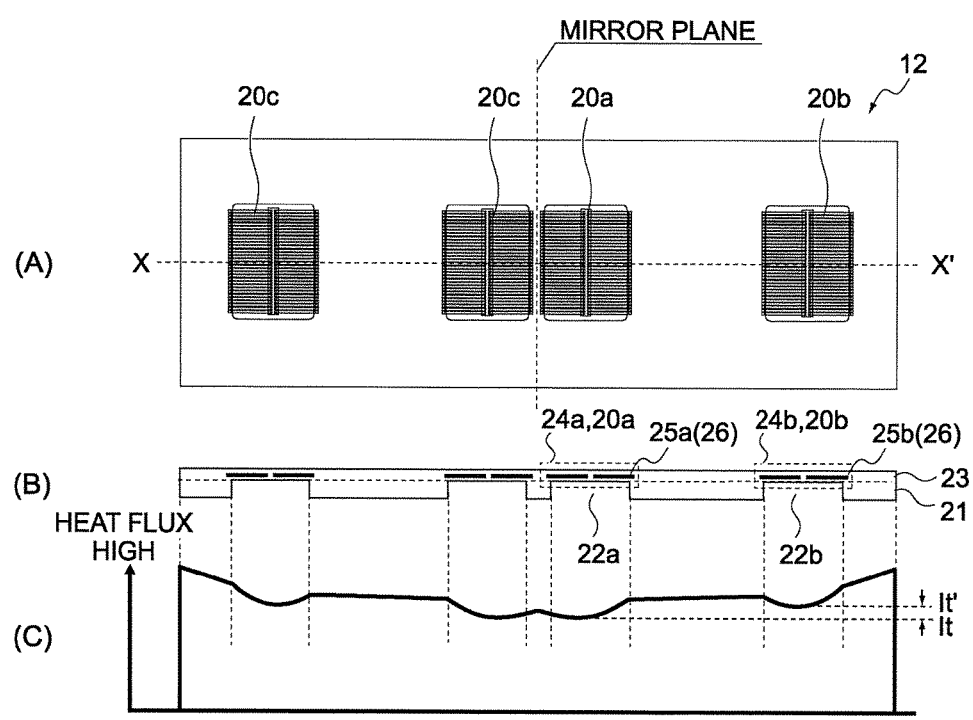
FIG. 7 is an explanatory diagram of the configuration and functions of a MEMS chip (second MEMS chip) included in an internal temperature measurement device according to a second embodiment of the present invention.

FIG. 7(A) illustrates a top view of the second MEMS chip 12, and FIG. 7(B) illustrates a cross-sectional view of the second MEMS chip 12 taken along the line X-X' in FIG. 7(A). FIG. 7(C) illustrates a distribution diagram of heat flux on the top surface of the second MEMS chip 12, which is released upward from the vicinity of the cross-section taken along the line X-X' in FIG. 7(A).

As illustrated in FIGS. 7(A) and 7(B), the second MEMS chip 12 includes four output cells 20 (20a, 20b, 20c) having substantially the same shape. The second MEMS chip 12 has a configuration in which a center plane in the left-right direction is a mirror plane.

The output cell 20a disposed in the vicinity of the mirror plane in the second MEMS chip 12 is a cell for measuring ΔT representing a heat flux It that is released upward from the lateral center part of the output cell 20a. The output cell 20c having a mirror relation with the output cell 20a is a cell provided in order to reduce the heat flux It.

The output cell 20b disposed at the right end of the second MEMS chip 12 is a cell for measuring ΔT' representing a heat flux It' that is released upward from the lateral center part of the output cell 20b. The output cell 20c having a mirror relation with the output cell 20b is a cell provided in order to obtain bilateral symmetry of the heat flux distribution (FIG. 7(C)) in the second MEMS chip 12 (to suppress increase in heat flux It due to bilateral asymmetry of heat flux distribution).

The second MEMS chip 12 with such arrangement of the output cells 20 enables, as illustrated in FIG. 7(C), the difference between the heat flux It and the heat flux It' to be a relatively large value (enables the It/It' value to be a relatively small value). Consequently, the internal temperature measurement device 10 according to the present embodiment also can measure the internal temperature of the measuring object more accurately with better responsiveness than hitherto.

The configuration employed for the second MEMS chip 12 can decrease It/It' without making the manufacturing of chips difficult or reducing the strength of the output cell 20a. Thus, it can be said that the internal temperature measurement device 10 according to the present embodiment including the second MEMS chip 12 is a device that is resistant to impact and is easily manufactured such that the estimation result of the internal temperature Tb is stabilized.

Third Embodiment

Now, the configuration of an internal temperature measurement device 10 according to a third embodiment of the present invention is described with reference to the same symbols used above for the description of the internal temperature measurement device 10 according to the first embodiment.

The internal temperature measurement device 10 according to the present embodiment is obtained by replacing the first MEMS chip 12 (see FIG. 4) in the internal temperature measurement device 10 according to the first embodiment with a third MEMS chip 12 having a configuration illustrated in FIG. 8.

As illustrated in FIG. 8, the third MEMS chip 12 has a configuration in which a center plane in the left-right direction and a center plane in the front-back direction (up-down direction in FIG. 8) are each a mirror plane. In each section partitioned by the two mirror planes in the third MEMS chip 12, an output cell 20a for measuring ΔT and an output cell 20b for measuring ΔT', which has substantially the same shape (same configuration) as the output cell 20a, are provided. The position of the output cell 20a in each section is determined such that four output cells 20a are adjacent to one another at the center part of the third MEMS chip 12.

As schematically illustrated in FIG. 8, the four output cells 20a in the third MEMS chip 12 are connected such that the sum of the outputs thereof (potential difference between output 1 and output 2) can be output. The four output cells 20b in the third MEMS chip 12 are also connected such that the sum of the outputs thereof (potential difference between output 3 and output 4) can be output.

The third MEMS chip 12 is provided with a reference potential terminal capable of measuring ½ of the sum of the outputs of the four output cells 20a when a potential difference between the reference potential terminal and the output 1 is measured and capable of measuring the remaining ½ of the sum of the outputs of the four output cells 20a when a potential difference between the reference potential terminal and the output 2 is measured. The reference potential terminal is also capable of measuring ½ of the sum of the outputs of the four output cells 20b when a potential difference between the reference potential terminal and the output 3 is measured and capable of measuring the remaining ½ of the sum of the outputs of the four output cells 20b when a potential difference between the reference potential terminal and the output 4 is measured.

The internal temperature measurement device 10 according to the present embodiment employs an ASIC 13 configured to generate data representing ΔT from a potential difference between the output 1 and the reference potential terminal and a potential difference between the output 2 and the reference potential terminal and generate data representing ΔT' from a potential difference between the output 3 and the reference potential terminal and a potential difference between the output 4 and the reference potential terminal.

Arranging the output cells 20a and 20b as illustrated in FIG. 8 enables a heat flux It that is released upward from a lateral center portion of each output cell 20a to have a value smaller than a heat flux It' that is released upward from a lateral center portion of each output cell 20b. The internal temperature measurement device 10 according to the present embodiment thus enables the internal temperature of a measuring object to be measured more accurately with better responsiveness than hitherto.

When the bottom surface of the base portion 11 is brought into contact with the surface of the measuring object for measurement of the internal temperature Tb, adhesion between a part of the bottom surface of the base portion 11 and the surface of the measuring object is sometimes low. The internal temperature measurement device 10 according to the present embodiment calculates the internal temperature Tb by using an average value of temperature differences measured by the four output cells 20a and an average value of temperature differences measured by the four output cells 20b. Consequently, the use of the internal temperature measurement device 10 enables the internal temperature Tb to be measured with almost no fear in that an internal temperature Tb greatly different from the original temperature is output due to low adhesion between a part of the bottom surface of the base portion 11 and the surface of the measuring object.

The configuration employed for the third MEMS chip 12 can decrease It/It' without making the manufacturing of chips difficult or reducing the strength of the output cell 20a. Thus, it can be said that the internal temperature measurement device 10 according to the present embodiment including the third MEMS chip 12 is a device that is resistant to impact and is easily manufactured such that the estimation result of the internal temperature Tb is stabilized.

Modification

The internal temperature measurement device 10 according to each of the embodiments described above can be variously modified. For example, the first MEMS chip 12 (FIG. 4) or the second MEMS chip 12 (FIG. 7) can be modified to have a structure without a thermopile 25 (that is, only a thin film portion) instead of including each output cell 20c.

The second MEMS chip 12 (FIG. 7) can be modified to a chip capable of outputting the sum of an output of the leftmost output cell 20c and an output of the output cell 20b and the sum of an output of the output cell 20a and an output of the adjacent output cell 20c.

As the arithmetic circuit 14, a circuit configured to calculate the internal temperature Tb by an expression different from Expression (e1). The arithmetic circuit 14 may be provided on the instrumentation device side.

The internal temperature measurement device 10 according to each embodiment can be modified to a device that is not connected to an instrumentation device when used (for example, a thermometer with a liquid crystal display on which the result of calculating an internal temperature by the arithmetic circuit 14 is displayed). It should be understood, for example, that the specific configuration of each output cell is not limited to the one described above and that the temperature sensor 18 may be provided on the output cell 20 or the base portion 11 separately from the ASIC 13.

REFERENCE SIGNS LIST

10 Internal temperature measurement device
11 Base portion
12 MEMS chip
13 ASIC
14 Arithmetic circuit
15 Terminal
16 Housing
18 Temperature sensor
20 Output cell
21 Substrate
22 Opening portion
23 Laminate portion
24 Thin film portion
25 Thermopile
26 Thermocouple

The invention claimed is:

1. An internal temperature measurement device, comprising:
a base portion, one surface of which is to be brought into contact with a surface of a measuring object when an internal temperature of the measuring object is measured;
a MEMS chip arranged on another surface of the base portion, and including: a substrate portion including a first thin film portion and a second thin film portion that are hollow on the base portion side; a first thermopile configured to measure a first temperature difference between a predetermined region and another region of the first thin film portion; and a second thermopile configured to measure a second temperature difference between a predetermined region and another region of the second thin film portion; and a calculation unit configured to calculate an internal temperature of the measuring object by using the first temperature difference measured by the first thermopile and the second temperature difference measured by the second thermopile, wherein the MEMS chip is configured such that a first heat flux which passes through the predetermined region of the first thin film portion from the measuring object in contact with the one surface of the base portion, and which is determined on the basis of the first temperature difference, and a second heat flux which passes through the predetermined region of the second thin film portion from the measuring object in contact with the one surface of the base portion, and which is determined on the basis of the second temperature difference, are different from each other, and in order to reduce the first heat flux, a thin film portion that is hollow on the base portion side is provided on at least one of both sides of the first thin film portion of the substrate portion in a direction where the first thin film portion and the second thin film portion are arranged.

2. The internal temperature measurement device according to claim 1, wherein the MEMS chip is configured such that it has a first mirror plane perpendicular to the direction where the first thin film portion and the second thin film portion are arranged, the first thin film portion, the second thin film portion, the first thermopile and the second thermopile are included in each part sectioned by the first mirror plane, and the first thin film portion in each part is adjacent to the first mirror plane.

3. The internal temperature measurement device according to claim 1, wherein:

the MEMS chip is configured such that it has a first mirror plane and a second mirror plane orthogonal to the first mirror plane, the first thin film portion, the second thin film portion, the first thermopile and the second thermopile are included in each part sectioned by the first and second mirror planes, and the first thin film portion in each part is adjacent to the first mirror plane and the second mirror plane; and the calculation unit calculates the internal temperature of the measuring object by using an average value of first temperature differences measured by four first thermopiles in the MEMS chip and an average value of second temperature differences measured by four second thermopiles in the MEMS chip.

* * * * *